(12) United States Patent
Staehle

(10) Patent No.: US 6,383,211 B1
(45) Date of Patent: May 7, 2002

(54) STENT PLACEMENT INSTRUMENT AND METHOD OF ASSEMBLY

(75) Inventor: Bradford G. Staehle, Minnetonka, MN (US)

(73) Assignee: American Medical Systems, Inc., Minnetonka, MN (US)

( * ) Notice: Subject to any disclaimer, the term of this patent is extended or adjusted under 35 U.S.C. 154(b) by 0 days.

(21) Appl. No.: 09/659,354

(22) Filed: Sep. 12, 2000

Related U.S. Application Data

(63) Continuation of application No. 09/114,012, filed on Jul. 10, 1998, now Pat. No. 6,143,021.

(51) Int. Cl.$^7$ .................................................. A61F 2/06
(52) U.S. Cl. ...................................... 623/1.11; 606/108
(58) Field of Search .............................. 623/1.11, 1.12; 606/108, 191, 194, 198, 195, 196, 199, 171, 39–50, 167

(56) References Cited

U.S. PATENT DOCUMENTS

| | | | |
|---|---|---|---|
| 5,571,136 A | * | 11/1996 | Weaver ...................... 606/205 |
| 5,591,172 A | * | 1/1997 | Bachmannn et al. ....... 606/108 |
| 5,591,222 A | | 1/1997 | Susawa et al. |
| 5,672,169 A | | 9/1997 | Verbeek |
| 5,700,269 A | | 12/1997 | Pinchuk et al. |

(List continued on next page.)

FOREIGN PATENT DOCUMENTS

| | | |
|---|---|---|
| EP | 0829242 | 3/1998 |
| WO | WO9807387 | 2/1998 |
| WO | WO9930763 | 6/1999 |
| WO | WO0010486 | 3/2000 |
| WO | WO0015143 | 3/2000 |
| WO | WO0018329 | 6/2000 |

Primary Examiner—Henry J. Recla
Assistant Examiner—Vy Q. Bui
(74) Attorney, Agent, or Firm—Oppenheimer Wolff & Donnelly LLP

(57) ABSTRACT

An instrument places a stent axially and is reusable with different size stents. A loop on an arm extends tangentially so at least one bore aligns axially. A tab extends from the arm axially and from the loop in a plane. A ring on a limb extends tangentially and has an axially aligned hole in a plane. A bracket extends from the tab over and in front of the limb. A tube extends for coaxial deposition axially, into the bore and the hole locating the ring forward of the loop. An end on the tube opposite the bore grips the stent. A sheath coaxial to the tube slides along the end and extends from the hole. A sheath cavity near the end is for the stent. A shaft in the plane attaches to the bracket parallel and axially conjugates with the limb and arm prevents rotation. An axial control in the arm for selective movement relative to the shaft adjusts the position of the shaft to the arm. A latch on the bracket secures the limb axially for loading and delivering the stent. A catch on the tab prevents release of the stent from the tube thus permitting the ring to fully approach the loop. At least one grip carried between the stent and its end engages the stent in the cavity. The latch and catch have spring loaded keys to engage a way on the limb for limiting movement of the ring to the loop. A method of assembling the instrument has steps of extending the tube to support the stent, locating the ring on the tube forward of the loop, sliding the sheath and accommodating the stent in the cavity within the end. Conjugating the shaft with the limb and the arm and moving the axial control for adjusting the shaft are steps. The method has the steps of securing the axial positions of the limb and bracket with the latch and selectively permitting the sheath relative to the tube for loading and thereafter delivering the stent. The steps of preventing stent release until manual release of the catch, permitting the ring to approach the loop, engaging the stent with the grip and disassembling via the latch and the catch are used. The steps of adjusting the shaft, engaging the receiving way for limiting axial movement, moving a lock of the axial control and extending the support fitted coaxially over and about the sheath are followed.

6 Claims, 4 Drawing Sheets

U.S. PATENT DOCUMENTS

| | | |
|---|---|---|
| 5,725,519 A | 3/1998 | Penner et al. |
| 5,749,921 A | 5/1998 | Lenker et al. |
| 5,800,517 A | 9/1998 | Anderson et al. |
| 5,810,873 A | 9/1998 | Morales |
| 5,911,752 A | 6/1999 | Dustrude et al. |
| 5,947,993 A | 9/1999 | Morales |
| 6,018,857 A | 2/2000 | Duffy et al. |
| 6,068,635 A | 5/2000 | Gianotti |
| 6,093,194 A | 7/2000 | Mikus et al. |
| 6,096,027 A | 8/2000 | Layne |
| 6,123,720 A | 9/2000 | Anderson et al. |
| 6,149,680 A | 11/2000 | Shelso et al. |
| 6,183,504 B1 | 2/2001 | Inoue |

\* cited by examiner

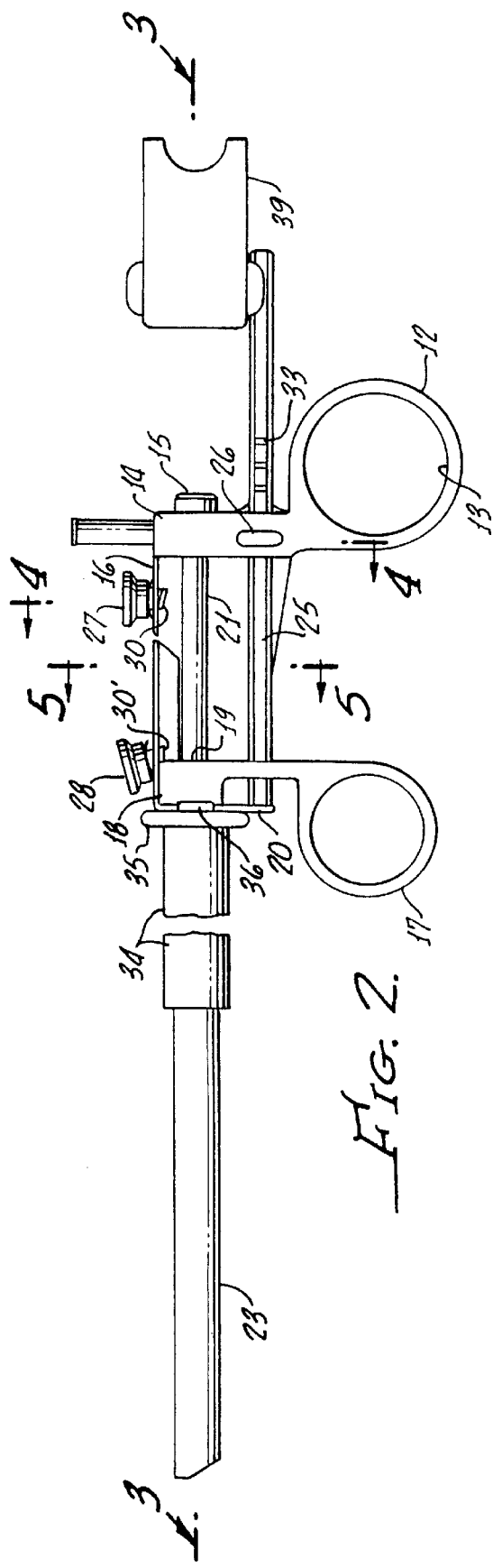
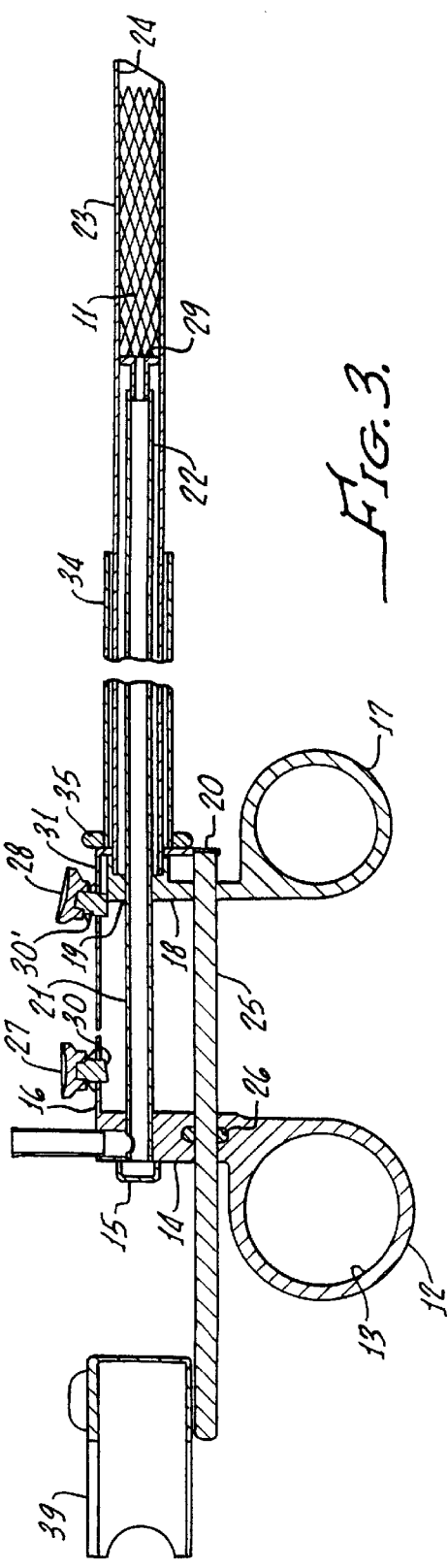

STENT PLACEMENT INSTRUMENT AND METHOD OF ASSEMBLY

RELATED APPLICATIONS

This application is a continuation of U.S. patent application Ser. No. 09/144,012, filed Jul. 10, 1998.

FIELD OF THE INVENTION

This relates to an instrument for use by a surgeon to place and/or remove a stent within and along an axis aligned with a patient's lumen. More particularly, the instrument can be loaded with a stent by the practitioner, is reusable because it is easily assembled and disassembled for cleaning, and sterilization.

BACKGROUND OF THE DISCLOSURE

Tubular prostheses for transluminal implantation in body canals, for example urethra or ureters, for the purpose of repair or dilation are known. These prostheses, referred to herein as stents, may be generally tubular elements. Stents are self expanding or are balloon expandable radially within a lumen to open therethrough a passage, herein all types of stents will be referred to as expanding stents.

A typical self-expanding stent is disclosed in U.S. Pat. No. 4,655,771, Which stent has a radially and axially flexible, elastic tubular body of a predetermined diameter that is variable under axial movement of ends of the body relative to each other. That stent has of a plurality of individually rigid but flexible and elastic thread elements defining a radially self-expanding helix. The disclosure in U.S. Pat. No. 4,655,771 is made is a part hereof and incorporated herein by reference.

Placement of the stent according to U.S. Pat. No. 4,665,771 in a body vessel is achieved by a device having a piston to push the stent or a latch to hook the stent and push or pull it into position.

U.S. Pat. No. 4,990,151 has an instrument for the implantation or extraction of a stent. The instrument has a plurality of internally held spring members that are released by withdrawal of an over tube. The members thus engage the inside of the urethra to expand the lumen so the spring members can be advanced over the stent and caused to engage the outside thereof whereupon the over tube is positioned to keep the members engaged. While this instrument comes apart for sterilization and reuse, it is not adjustable for different size stents and was made to use for explantation.

U.S. Pat. No. 4,768,507 has a mandrel for carrying a spring helix inside a tube and is delivered by removing the tube so the helix spring can unwind and expand. It is shown as a disposable instrument.

U.S. Pat. No. 5,026,377 describes and claims in combination, a self-expanding braided stent as in '771 and an instrument for the deployment or retraction in a body canal of the stent. The instrument has an elongated tubular outer sleeve with proximal and distal ends, an elongated core in the sleeve is movable relative thereto so the core which is longer than the sleeve includes a grip member at or near its distal end. The grip member is on the core to: (I) releasably hold the self expanding stent within the outer sleeve, (ii) deploy the stent beyond the distal end of the outer sleeve when the outer sleeve is moved in a backward direction relative to the core and (iii) retract the stent back within said outer sleeve when the core is pulled in a backward direction relative to the outer sleeve.

European Patent Number EP 0 518 838 A1 has a transluminal implantation device for an implantation of substantially tubular, radially expandable stent. The device has a central tube or shaft surrounded by an outer tube axially displaceable relative said central tube or shaft, the radial dimensions of the tubes or tube and shaft forming an annular space therebetween for holding the stent in an unexpanded state. The held stent can be axial displaced from the outer tube relative to said central tube or shaft at a distal end thereof. There is an undercut groove forming a circumferential flange wherein the proximal end of the stent rests until release with rearward displacement of the outer tube.

It has now been found that a reusable deployment instrument for implanting a variety of stent designs and configurations may be needed to reduce the cost and expense of medical care. The need to sterilize and adjust the instrument has not been solved by the disposable deployment devices available. Moreover it is not a simple matter to revise such disposable tools to be used for more than one time. Manufactures of those disposable devices strive to make such tools difficult or impossible to reuse.

This invention relates to a reusable instrument for the placement of a stent in a body canal, and means for positioning and releasing the stent.

SUMMARY OF THE INVENTION

An instrument for use by a surgeon to place within and remove from a patient's lumen a stent aligned along an axis is preferably reusable in that it can be disassembled for cleaning and may be reloaded with a new stent. The instrument is also adjustable for stents of different sizes. A thumb loop for manipulation by a surgeon may have an open center into which the surgeon's thumb may fit when it is normal to the axis. An arm extending tangentially from the thumb loop is preferably in a plane with the axis. The arm may perhaps have at least one bore in alignment with the axis. A tab extends from the arm along the axis and from the thumb loop so the arm, tab and thumb loop reside substantially in the plane with one another and the axis.

A finger ring for manipulation by a surgeon could be centrally open to receive the surgeon's finger. A limb extends tangentially from the finger ring and is preferably attached thereto. The limb can include an axially aligned hole so the hole, finger ring and the limb may be positioned in the plane with the axis. A front bracket extends from the tab over and in front of the limb. A tube to support the stent could be located for extending therefrom. The tube may be positioned for coaxial deposition about the axis, into the bore and the hole, the tube for locating the finger ring forward of the thumb loop. The location of the tube is preferably for ergonomic use by the surgeon in a sliding action of the finger ring relative to the tube when guided along axis.

A stent end can be on the tube opposite where the tube fits bore for gripping the stent in the sheath for delivery. A sheath might be for sliding along the stent end on the tube when the sheath extends from the hole along the axis and toward the stent end. The sheath is most preferably coaxially disposed about the tube. A cavity in the sheath beyond the stent end on the tube may be included for accommodating the stent being carried along the axis cantilever from the stent end on the tube. A shaft positioned in the plane could be attached to the front bracket. The shaft may be generally parallel to the axis so the shaft conjugates with the limb and arm to prevent relative rotary motion between them with respect to the axis.

An axial control preferably fits within the arm for selective movement by the surgeon relative to the shaft. The axial control is preferred for adjusting the axial position of the shaft relative to the arm. Thus the axial control can be used for setting the axial position of the shaft with respect to the arm to thereby adjust the instrument for stents of various lengths. A latch on the front bracket may be to secure the relative axial positions of the limb and the front bracket. The latch can be used to selectively permit the surgeon to move the sheath relative to the tube for loading and thereafter delivering the stent. A catch on the tab may be included to prevent complete release of the stent from the tube without the prior manual release of the catch thus permitting the finger ring to fully approach the thumb loop.

At least one grip can be carried between the stent and the stent end for engaging the stent reduced to a diameter to fit within the cavity before and during placement and/or removal from the patient's lumen. The at least one grip is most preferably operatively mounted in the sheath near the stent end for axially locating precisely the stent within the patient's lumen for release. The axial control, the latch and the catch are in the preferred embodiment all positioned relative to the shaft and the tab and the front bracket, respectively so the instrument may either be disassembled for cleaning and sterilization or assembled and adjusted to a particular stent length. The latch might include a spring loaded key on the front bracket and the catch can have a spring loaded key on the tab. Each spring loaded key is most preferably positioned to cooperatively engage a receiving way atop the limb for limiting the axial movement of the finger ring relative to the thumb loop.

The axial control might include a lock for transverse movement by the surgeon relative to the arm. The shaft may have settings for cooperative engagement with the lock to define preset adjustment locations for accommodating stents of various lengths. A support might be fit coaxially over and about the sheath. The support preferably extends along the sheath from the front bracket so that axial movement of the sheath may be independent of the support. A flange can be on the support for abutting the front bracket and a tang on the abutted flange resiliently engages the front bracket to restrain axial movement of the flange away from the front bracket. The axial control may alternately include a pinion carried on the arm for rotary movement by the surgeon relative to a rack on the shaft for setting the adjustment locations of the tube relative to the sheath for accommodating stents of various lengths.

An adapter preferably abuts the arm and extends away from the patient and toward the surgeon. The adapter can be shaped for permitting sliding engagement relative to the shaft. An extension may be fit within the arm and over the shaft in parallel relation to the adapter. The extension might be for supporting the sliding engagement of the adapter with the arm along the shaft when directed away from the stent end. The latch and the catch preferably hold the limb from axial motion toward the surgeon but may be manually released for such axial movement and automatically permit axial limb motion away from the surgeon.

A method of assembling and disassembling an instrument for use by a surgeon to place a stent within a patient's lumen has operating steps. Extending a tube to support the stent in coaxial disposition about the axis, into the bore and the hole is a step of the preferred method. The method may have the step of locating the finger ring on the tube forward of the thumb loop for ergonomic use by the surgeon in a sliding action of the finger ring relative to the tube when guided along axis. Sliding a sheath extending from the hole and coaxially disposed about the tube may be a step. The method step of accommodating the stent in a cavity within the sheath and along the axis can be included. Conjugating a shaft positioned attached to the front bracket and parallel to the axis with the limb and the arm to prevent relative rotary motion between them with respect to the axis might be followed. The method could include moving an axial control fit within the arm and adjusting the axial position of the shaft relative to the arm for setting the axial position of the shaft with respect to the arm to thereby changing the instrument for stents of various lengths. The method preferably has the step of securing the relative axial positions of the limb and the front bracket with a latch on the front bracket and selectively permitting the surgeon to move the tube relative to the sheath for loading and thereafter delivering the stent. The step of preventing complete release of the stent from the tube without the prior manual release of a catch on the tab and thereby permitting the finger ring to fully approach the thumb loop is in the method.

The step of engaging with a grip the stent reduced to a diameter to fit within the cavity before and during placement and/or removal from the patient's lumen is part of the method. The method step of disassembling via the latch and the catch the instrument for sterilization is preferred. The method may include the step of adjusting the shaft to a particular stent length with the axial control. The step of cooperatively engaging a receiving way atop the limb for limiting the axial movement of the finger ring relative to the thumb loop with a spring loaded key on the front bracket and with a spring loaded key on the tab can be performed. The method step of moving a lock of the axial control transversely relative to the arm and the shaft to define preset adjustment locations for accommodating stents of various lengths is preferred. The step of the method of extending a support fitted coaxially over and about the sheath is followed.

BRIEF DESCRIPTION OF THE DRAWINGS

FIG. 2 is a side elevation view of the instrument of FIG. 1 but the view discloses the side opposite that shown in FIG. 1.

FIG. 3 is a said e view of the instrument shown in cross section and as would be seen along line 3—3 in FIG. 2.

DETAILED DESCRIPTION OF THE INVENTION

Figure 1:
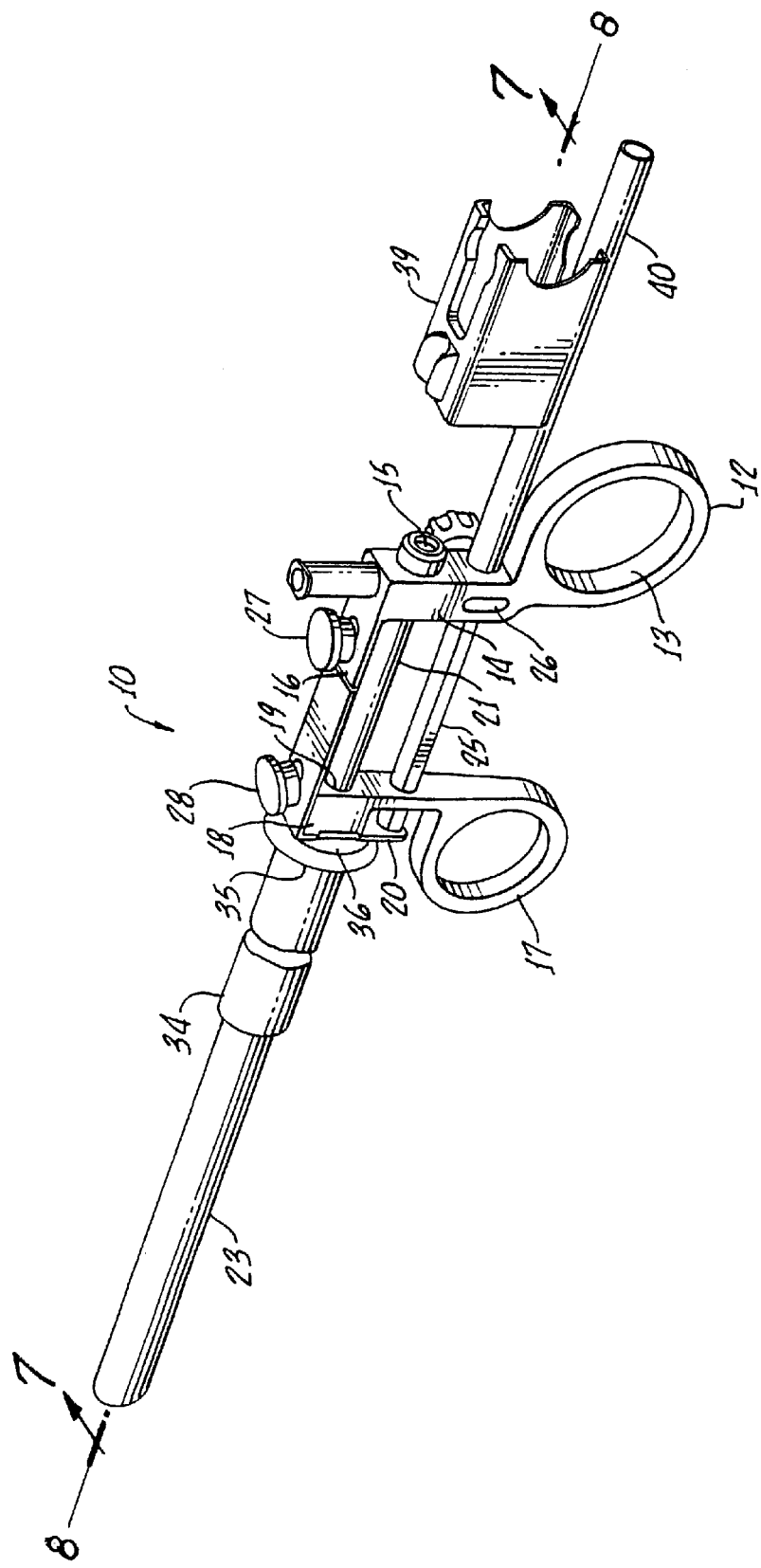
FIG. 1 is a perspective view of an instrument for use by a surgeon to place and remove an expandable stent within and along an axis aligned with a patient's lumen.

An instrument 10 for use by a surgeon to place within and remove from a patient's lumen a stent 11 aligned along an axis 8—8 is shown in FIGS. 1 and 3. The instrument 10 is reusable in that it can be disassembled for cleaning and may be reloaded with a new stent 11. Tools are not required to disassemble the instrument 10 for cleaning. The instrument 10 is also adjustable for stents 11 of different sizes. A thumb loop 12 for manipulation by a surgeon has an open center 13 into which the surgeon's thumb may fit when it is normal to the axis 8—8. An arm 14 extending tangentially from the thumb loop 12 is preferably in a plane with the axis 8—8. The arm 14 has at least one bore 15 in alignment with the axis 8—8. A tab 16 extends from the arm 14 along the axis 8—8 and from the thumb loop 12 so the arm 14, tab 16 and thumb loop 12 reside substantially in the plane with one another and the axis 8—8.

A finger ring 17 for manipulation by a surgeon could be centrally open to receive the surgeon's finger. A limb 18 extends tangentially from the finger ring 17 and is preferably attached thereto in FIG. 1. The limb 18 can include an axially aligned hole 19 so the hole 19, finger ring 17 and the limb 18 may be positioned in the plane with the axis 8—8. A front bracket 20 extends from the tab 16 over and in front of the limb 18. A tube 21 to support the stent 11 could be located for extending from arm 14. The tube 21 may be positioned for coaxial deposition about the axis 8—8, into the bore 15 and the hole 19, the tube 21 locates the finger ring 17 forward of the thumb loop 12. The location of the tube 21 is preferably for ergonomic use by the surgeon in a sliding action of the finger ring 17 relative to the tube 21 when guided along axis 8—8.

Figure 7:
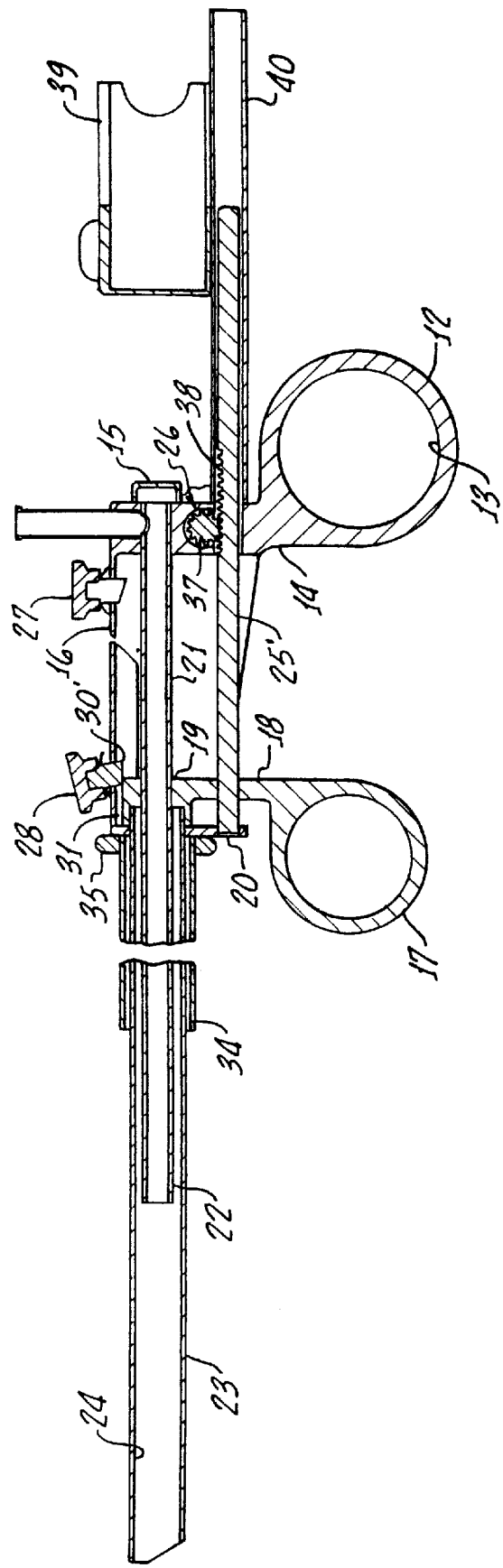
FIG. 7 is a side view of the instrument containing rack and pinion axial control shown in cross section as would be seen along line 7—7 in FIG. 1.

A stent end 22 can be on the tube 21, see FIGS. 3 and 7, opposite where the tube 21 fits bore 15 for gripping the stent 11 during delivery. A sheath 23 slides along the stent end 22 on the tube 21 when the sheath 23 extends from the hole 19 along the axis 8—8 and toward the stent end 22. The sheath 23 is preferably coaxially disposed about the tube 21. A cavity 24 in the sheath 23 beyond the stent end 22 on the tube 21 is included for accommodating the stent 11 being carried along the axis cantilever in cross section [FIGS. 3 and 7] from the stent end 22 on the tube 21. A shaft 25 positioned in the plane is attached to the front bracket 20. The shaft 25 is generally parallel to the axis 8—8 so the shaft 25 conjugates with the limb 18 and arm 14 to prevent relative rotary motion between them with respect to the axis 8—8.

An axial control 26 fits within the arm 14 for selective movement by the surgeon relative to the shaft 25. The axial control 26 is for adjusting the axial positions of the shaft 25 relative to the arm 14. Thus the axial control 26 can be used for setting the axial positions of the shaft 25 with respect to the arm 14 to thereby adjust the instrument 10 for stents 11 of various lengths. A latch 28 on the front bracket 20 secures the relative axial positions of the limb 18 and the front bracket 20. The latch 28 can be used to selectively permit the surgeon to move the sheath 23 relative to the tube 21 for loading and thereafter delivering the stent 11, FIGS. 1, 3 and 7. A catch 27 on the tab 16 is included to prevent complete release of the stent 11 from the tube 21 without the prior manual release of the catch 27 thus permitting the finger ring 17 to fully approach the thumb loop 12. see FIGS. 1, 2, 3, 5 and 7.

Figure 4:
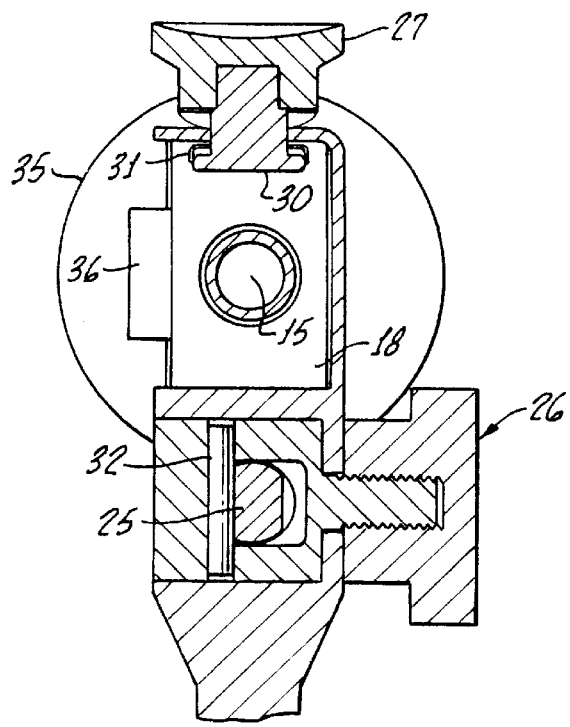
FIG. 4 is an enlarged end elevational view in cross section as would be seen along lines 4—4 of FIG. 2.
Figure 5:
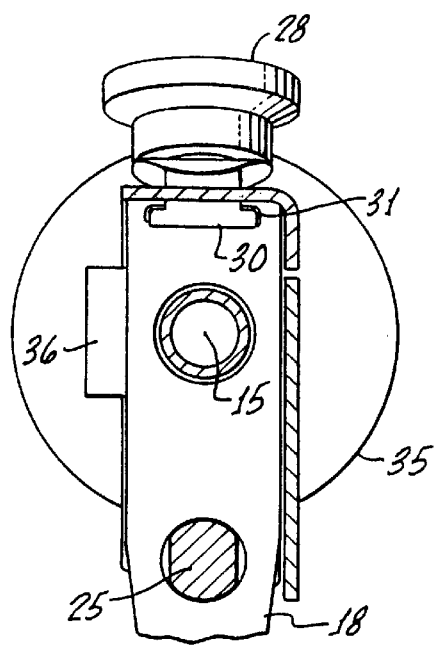
FIG. 5 is an end elevational view in cross section taken along lines 5—5 of FIG. 2.

At least one grip 29 in FIG. 3 can be carried between the stent 11 and the stent end 22 for engaging the stent 11 reduced to a diameter to fit within the cavity 24 before and during placement and/or removal from the patient's lumen. The at least one grip 29 is operatively mounted in the sheath 23 near the stent end 22 for axially locating precisely the stent 11 within the patient's lumen for release. The axial control 26, the latch 28 and the catch 27 are in the preferred embodiment all positioned relative to the shaft 25 and the tab 16 and the front bracket 20, respectively so the instrument 10 may either be disassembled for cleaning and sterilization or assembled and adjusted to a particular stent 11 length. The catch 27 includes a spring loaded key 30 in FIG. 4 on the tab 16 and the latch 28 has a spring loaded key 30' on the front bracket 20 in FIG. 5. Each spring loaded key 30 or 30' is positioned to cooperatively engage a receiving way 31 or 31' atop the limb 18 for limiting the axial movement of the finger ring 17 relative to the thumb loop 12.

The axial control 26 includes a lock 32 for transverse movement by the surgeon relative to the arm 14. The shaft 25 may have settings 33 for cooperative engagement with the lock 32 to define preset adjustment locations for accommodating stents 11 of various lengths. A support 34 fits coaxially over and about the sheath 23. The support 34 preferably extends along the sheath 23 from the front bracket 20 so that axial movement of the sheath 23 may be independent of the support 34. A flange 35 in FIGS. 1, 2, 3, 4, 5 and 7 can be on the support 34 for abutting the front bracket 20 and a tang 36 on the abutted flange 35 resiliently engages the front bracket 20 to restrain axial movement of the flange 35 away from the front bracket 20.

Figure 6:
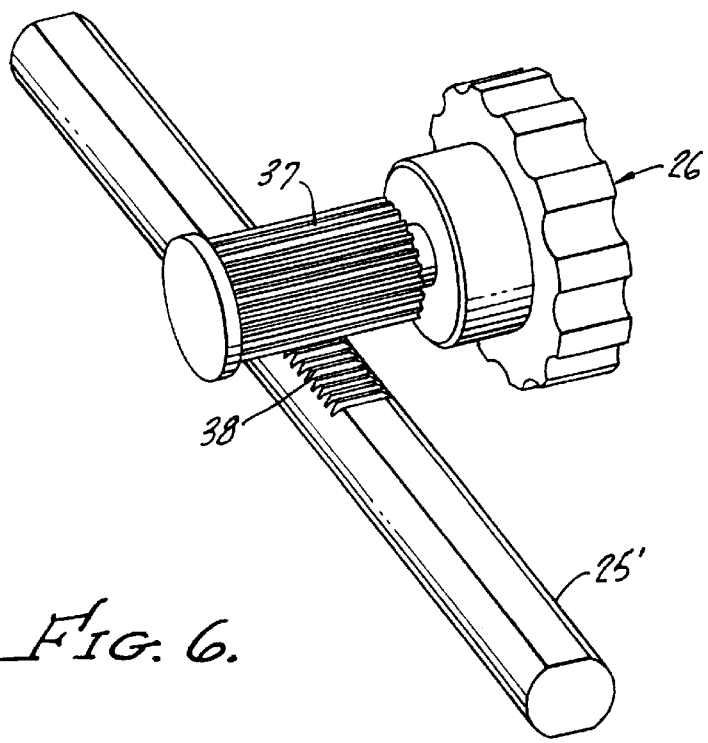
FIG. 6 is a perspective view of an alternate rack and pinion axial control for use with the instrument of FIG. 1.

The axial control 26 may alternately include a pinion 37 in FIGS. 6 and 7 carried on the arm 14 for rotary movement by the surgeon relative to a rack 38 on the shaft 25' for setting the adjustment locations of the tube 21 relative to the sheath 23 for accommodating stents 11 of various lengths.

An adapter 39 preferably abuts the arm 14 and extends away from the patient and toward the surgeon. The adapter 39 can be shaped for permitting sliding engagement relative to the shaft 25 or 25'. An extension 40 may be fit within the arm 14 and over the shaft 25 or 25' in parallel relation to the adapter 39. The extension 40 supports the sliding engagement of the adapter 39 with the arm 14 along the shaft 25 or 25' when directed away from the stent end 22. The latch 28 and the catch 27 hold the limb 18 preventing axial motion toward the surgeon but may be manually released for such axial movement and automatically permit axial limb 18 motion away from the surgeon.

A method of assembling and disassembling instrument 10 for use by a surgeon to place stent 11 within a patient's lumen has operating steps. Extending tube 21 to support the stent 11 in coaxial disposition about the axis 8—8, into the bore 15 and the hole 19 is a step of the preferred method. The method may have the step of locating the finger ring 17 on the tube 21 forward of the thumb loop 12 for ergonomic use by the surgeon in a sliding action of the finger ring relative to the tube 21 when guided along axis 8—8. Sliding sheath 23 extending from the hole 19 and coaxially disposed about the tube 21 is a step. The method step of accommodating the stent 11 in cavity 24 within the sheath 23 and along the axis 8—8 is included. Conjugating shaft 25 or 25' positioned attached to the front bracket 20 and parallel to the axis 8—8 with the limb 18 and the arm 14 to prevent relative rotary motion between them with respect to the axis 8—8 is followed. The method includes moving axial control 26 fit within the arm 14 for adjusting the axial position of the shaft 25 or 25' relative to the arm 14 for setting the axial position of the shaft 25 or 25' with respect to the arm 14 to thereby changing the instrument 10 for stents 11 of various lengths. The method has the step of securing the relative axial positions of the limb 18 and the front bracket 20 with catch 27 on the tab 16 and selectively permitting the surgeon to move the tube 21 relative to the sheath 23 for loading and thereafter delivering the stent 11. The step of preventing complete release of the stent 11 from the tube 21 without the prior manual release of latch 28 on front bracket 20 and thereby permitting the finger ring 17 to fully approach the thumb loop 12 is in the method.

The step of engaging with grip 29 the stent 11 reduced to a diameter to fit within the cavity 24 before and during placement and/or removal from the patient's lumen is part of the method. The method step of disassembling via the latch 28 and the catch 27 the instrument 10 for sterilization is preferred. The method includes the step of adjusting the shaft 25 or 25' to a particular stent 11 length with the axial control 26. The step of cooperatively engaging receiving way 31 atop the limb 18 for limiting the axial movement of the finger ring 17 relative to the thumb loop 12 with spring loaded key 30' on the front bracket 20 and with spring loaded key 30 on the tab 16 is performed. The method step of moving lock 32 of the axial control 26 transversely relative to the arm 14 and the shaft 25 to define preset adjustment locations or setting 33 for accommodating stents 11 of various lengths is performed. The step of the method of extending support 34 fitted coaxially over and about the sheath 23 is followed.

Skilled artisans will no doubt appreciate that stents 11 of various constructions, materials, diameters and lengths can be used with the instrument 10 and method disclosed. Any material approved for medical use and resterilization is acceptable but medical grade stainless steel is preferred for its toughness and erosion resistance. Titanium, aluminum or reinforced polymers are also acceptable for the components disclosed and described. The instrument 10 is designed to be used with commercial scopes for interluminally viewing during stent 11 placement and/or removal. While self expanding stents 11 are preferred there is no reason that expandable stents 11 of various types cannot also be delivered and placed. Similarly stent grafts can be gripped, held and deployed with the instrument 10 and by the method as the coatings on the stent graft will not interfere with its use. While a particular preferred embodiment and alternates have been illustrated and described the scope of protection sought is in the claims that follow.

What is claimed is:

1. A method of deploying a stent comprising:

connecting a stent of predetermined length to one end of a stent retention shaft;

establishing a maximum space for relative movement of said stent retention shaft and a protective sheath by limiting relative movement of said stent retention shaft and said protective sheath to a specified region on a conjugating shaft, said maximum space being dependent on the length of said stent of predetermined size;

enclosing said stent in said protective sheath through relative movement between said stent retention shaft and said sheath, wherein said relative movement is achieved by using a finger ring connected to said protective sheath and a thumb ring connected to said retention shaft;

directing said stent retention shaft to a target site;

exposing said stent at said target site through relative movement of said stent retention shaft and said sheath;

preventing release of said stent from said stent retention shaft until performing a stent confirmation act on said shaft; and, releasing said stent from said retention shaft after performing said confirmation act.

2. A method as set forth in claim 1 wherein preventing release of said stent includes preventing relative movement of said retention shaft and said sheath.

3. A method as set forth in claim 2, wherein said confirmation act comprises enabling further relative movement of said retention shaft and said sheath.

4. A method as set forth in claim 2, wherein preventing release of said stent includes encountering a stop member which prevents relative movement of said retention shaft and said sheath.

5. A method as set forth in claim 4, wherein said confirmation act includes removing said stop member.

6. A method as set forth in claim 1, wherein said relative movement includes moving said sheath and holding said retention shaft stationary.

* * * * *